US011866401B2

United States Patent
Yang et al.

(10) Patent No.: US 11,866,401 B2
(45) Date of Patent: Jan. 9, 2024

(54) SALICYL FUMARATE DERIVATIVE AND ITS APPLICATION IN THE TREATMENT OF PARKINSON'S DISEASE AND OTHER NEURODEGENERATIVE DISEASES

(71) Applicant: CHONGQING NEUROPARK BIOSCIENCE CO., LTD., Chongqing (CN)

(72) Inventors: Lichuan Yang, New York, NY (US); Bobby Thomas, Augusta, GA (US); Mingyue Guo, Chongqing (CN)

(73) Assignee: CHONGQING NEUROPARK BIOSCIENCE CO., LTD., Chongqing (CN)

( * ) Notice: Subject to any disclaimer, the term of this patent is extended or adjusted under 35 U.S.C. 154(b) by 0 days.

(21) Appl. No.: 17/105,948

(22) Filed: Nov. 27, 2020

(65) Prior Publication Data

US 2021/0179533 A1 Jun. 17, 2021

Related U.S. Application Data

(63) Continuation of application No. 16/485,487, filed as application No. PCT/CN2018/078618 on Mar. 9, 2018, now abandoned.

(30) Foreign Application Priority Data

Mar. 28, 2017 (CN) .......................... 201710191351.9

(51) Int. Cl.
*C07C 69/60* (2006.01)
(52) U.S. Cl.
CPC .................... *C07C 69/60* (2013.01)
(58) Field of Classification Search
CPC .................... C07C 69/60; C07C 67/29
See application file for complete search history.

(56) References Cited

U.S. PATENT DOCUMENTS

2014/0194427 A1 7/2014 Chao

FOREIGN PATENT DOCUMENTS

| CN | 104710314 A | 6/2015 |
| CN | 105142628 A | 12/2015 |
| WO | 2014/052889 A1 | 4/2014 |

OTHER PUBLICATIONS

RN1564147-47-2, registry database compound, 2014.*
Jun. 15, 2018 International Search Report issued in International Patent Application No. PCT/CN2018/078618.
Jun. 15, 2018 Written Opinion issued in International Patent Application No. PCT/CN2018/078618.
Recasens, A. et al. "Lewy body extracts from Parkinson disease brains trigger-synuclein pathology and neurodegeneration in mice and monkeys." Annals of Neurology, vol. 75, No. 3, 2014, pp. 351-362.
Unterberger, U. et al. "Detection of disease-associated alpha-synuclein in the cerebrospinal fluid: a feasibility study." Neurobiology of Disease, vol. 33, No. 5, 2014, pp. 329-334.
Ahuja, M. et al. "Distinct Nrf2 Signaling Mechanisms of Fumaric Acid Esters and Their Role in Neuroprotection against 1-Methyl-4-Phenyl-1,2,3,6-Tetrahydropyridine Induced Experimental Parkinson's-Like Disease." The Journal of Neuroscience, vol. 36, No. 23, 2016, pp. 6332-6351.
RN1564147-47-2, 2014, registry database compound.
May 26, 2020 Office Action Issued in U.S. Appl. No. 16/485,487.

* cited by examiner

*Primary Examiner* — Sun Jae Yoo
(74) *Attorney, Agent, or Firm* — Oliff PLC

(57) ABSTRACT

A salicyl fumarate derivative having the general structural formula (A):

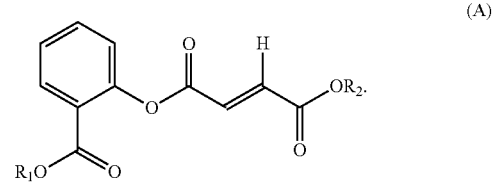

(A)

Figure 1:
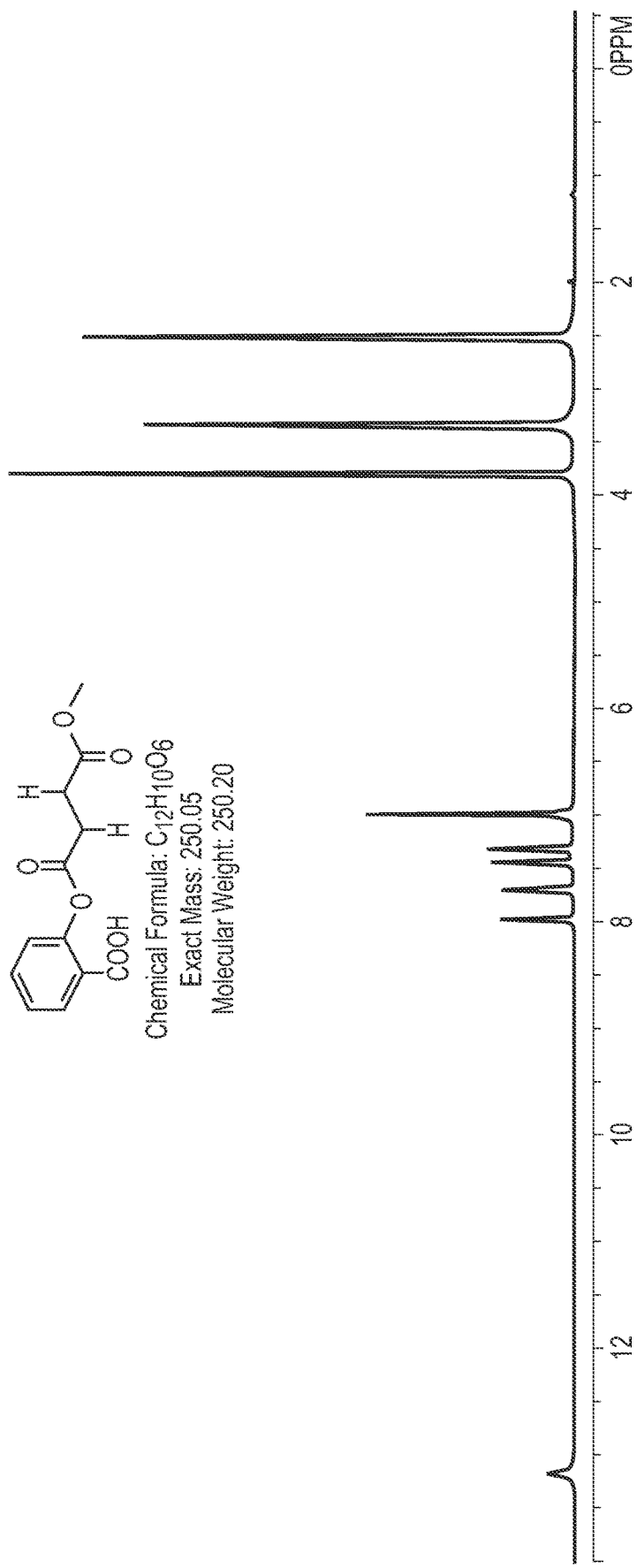

In the structural formula (A), $R_1$ is one of $H^+$, $Na^+$, $K^+$ or $NH_4^{+}$. $R_2$ is one of fumaric acid ester products. The derivative has the general structural formula of the combination of salicylic acid and fumaric acid through an esterification reaction. This category of compounds possesses good effects in treatment of neurodegenerative diseases.

2 Claims, 8 Drawing Sheets

SALICYL FUMARATE DERIVATIVE AND ITS APPLICATION IN THE TREATMENT OF PARKINSON'S DISEASE AND OTHER NEURODEGENERATIVE DISEASES

This Application is a Continuation of U.S. application Ser. No. 16/485,487 filed Aug. 13, 2019, which in turn is a National Stage Application of PCT/CN2018/078618 filed Mar. 9, 2018, which claims the benefit of Chinese Application No. 201710191351.9 (filed Mar. 28, 2017). The disclosures of the prior applications are hereby incorporated by reference herein in their entireties.

TECHNOLOGY AREA

This invention provides a new class of compounds, more specifically relates to a salicyl fumarate derivative, and its application in the treatment of Parkinson's Disease (referred to as PD hereafter).

TECHNOLOGY BACKGROUND

Neurodegenerative disease refers to a category of diseases in which neurons in the brain and the spinal cord are progressively lost. The brain and the spinal cord are made up of neurons, which have different functions, such as controlling movement, handling sensory information, and making decisions. Cells in the brain and spinal cord are generally not regenerated, so excessive damage on the neurons can be devastating and irreversible. Neurodegenerative diseases are caused by the loss of neurons or their myelin sheath, which worsens over time to lead to dysfunction. Neurodegenerative diseases mainly manifest into two aspects: one is movement disorder, such as cerebellar ataxia, the other is memory dysfunction and its related dementia.

As aging in population intensifies, the rate of occurrence of neurodegenerative diseases is also climbing. Neurodegenerative disease is a diseased state in which neurons in the brain and spinal cord are lost, where neuronal cells generally do not regenerate. Excessive damage can be devastating and irreversible. Neurodegenerative diseases worsen over time, eventually leading to dysfunction. Alzheimer's Disease and Parkinson's Disease are the two diseases with the highest prevalence, causing great pain to patients as well as their families.

Previous studies have shown that neurons can absorb injected α-synuclein proteins in both in vitro and in vivo models to form Lewy body proteins which are PD's characteristics. In 2014 Recasens et al. published that when Lewy bodies extracted from the substantia nigra of PD patients were injected into the substantia nigra or striatum of mice and rhesus monkeys, α-synuclein protein accumulated in host neurons. After 4-17 months, the dopaminergic neuron terminals appeared neurodegenerative, similar to PD pathology. They published the findings in Annals of Neurology (2014) (Publication information: Recasens A, Dehay B, Bove J, et al. Lewy body extracts from Parkinson disease brains trigger-synuclein pathology and neurodegeneration in mice and monkeys. Annals of Neurology. 2014, 75:351-362.)

In the same year, Unterberger et al. proposed a new mechanism, which is how α-synuclein spreads amongst neurons in PD. This team used an antibody that can distinguish between normal and abnormal α-synuclein in order to confirm how the pathological protein migrate to neighboring neurons. The same team also used antibodies to detect abnormal α-synuclein proteins in cerebrospinal fluid. This method will help early PD diagnosis and diagnoses of other α-synuclein diseases. It was published in Neurobiology of Disease (2014) (Publication information: Unterberger U, Lachmann I, Voitlander T. et al. Detection of disease-associated alpha-synuclein in the cerebrospinal fluid: a feasibility study. Neurobiology of Disease. 2014, 33:329-334.)

Chao J provided a technical scheme concerning a type of fumaric acid and its derivative, and acquired American patent authorization (Bulletin No.: US20140194427A1). In the technical scheme, the fumaric acid derivative provided by Chao J had a specific structural formula as shown in Figure (I). Chao J claimed the demonstrated fumaric acid derivative has treatment properties against neurodegenerative diseases, such as multiple sclerosis (MS), amyotrophic lateral sclerosis, PD, Huntington's Disease, or Alzheimer's Disease.

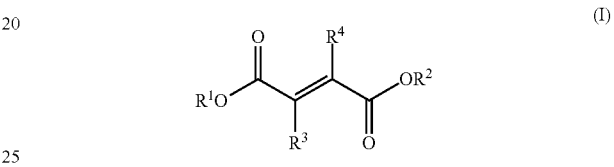

(I)

The USA FDA has approved a new twice-daily orally administered drug dimethyl fumarate (DMF, commercially known as Tecfidera) to be used to treat relapsing-remitting multiple sclerosis (RRMS). DMF has become one of the many approved treatments for MS. According to the National Multiple Sclerosis Society archives, two dosage forms of Interferon β-1a (Avonex and Rebif) as well as two dosage forms of β-1b (Betaseron and Extavia) have already been approved for RRMS therapy. Other drugs approved include Glatiramer acetate (Copaxone), Fingolimod (Gilenya) and Teriflunomide (Aubagio). Natalizumab (Tysabri) has received approval as well, but with conditional restrictions. Mitoxantrone (Novantrone) is approved to treat secondary progressive, progressive recurrent, and recurrent remission types of MS. Dalfampridine (Ampyra) is approved for improving the movement of MS patients.

Biogen Idec claims that, in the study called DEFINE, DMF users in MS patients have shown a 49% and 38% reduction in occurrences of recurrence and disability, while in the study called CONFIRM, DMF users have shown a 34% reduction in recurrence. Both studies illustrate that, compared to placebo, DMF can significantly reduce brain injury. Dr. Robert Fox from Cleveland Clinic Multiple Sclerosis Mellen Center claimed in a Biogen Idec report: "In clinical trials, compared to the placebo group, disease activity in DMF patients decreases, whether they are early-stage MS patients or more progressed patients. This drug provides doctors with another important treatment option to target MS patients of different stages."

However, FDA notes that DMF can lower the lymphocyte counts, though there is no evidence to suggest an increase in infections in DMF users. They suggest monitoring patient lymphocyte counts before and after treatment. Reddened face and gastrointestinal distress are the most common side effects.

Ahuja M et al. demonstrated the effect of DMF and its active metabolite monomethyl fumarate (MMF) on the Nrf2 signaling pathway as well as on 1-methyl-4-phenyl-1,2,3,6-tetrahydropyridine (MPTP)-induced mouse PD models. Their study confirmed that DMF and MMF exhibit protective effects against the neural toxicity of MPTP in mouse PD models. This is due to their unique Nrf2-mediated antioxidant, anti-inflammatory, and enhancement of mitochondrial functions. Unlike DMF, MMF does not consume glutathione and inhibit mitochondrial and glycolysis functions. The pathogenesis of PD includes oxidative damage, inflammation, and mitochondrial dysfunction. Ahuja M et al. claimed that MMF is the true active ingredient for treating PD. Their findings were published in The Journal of Neuroscience in 2016 (Publication information: Manuj Ahuja, Navneet Ammal Kaidery, Lichuan Yang, Noel Calingasan, Natalya Smirnova, Arsen Gaisin, Irina N. Gaisina, Irina Gazaryan, Dmitry M. Hushpulian, Ismail Kaddour-Djebbar, Wendy B. Bollag, John C. Morgan, Rajiv R. Ratan, Anatoly A. Starkov, M. Flint Beal, and Bobby Thomas. Distinct Nrf2 Signaling Mechanisms of Fumaric Acid Esters and Their Role in Neuroprotection against 1-Methyl-4-Phenyl-1,2,3, 6-Tetrahydropyridine Induced Experimental Parkinson's-Like Disease. The Journal of Neuroscience. 2016, 36(23): 6332-6351.)

CONTENT OF INVENTION

Based on early research discoveries and considering the side effects of DMF, the applicants invented a brand-new class of compounds and verified good activity the compounds have on Parkinson's disease (PD) models, which may also apply to other neurodegenerative diseases such as Alzheimer's disease (AD), and Huntington's disease (HD).

The new compounds provided by the applicants are salicyl fumarate derivatives. Its general structural formula (A) is:

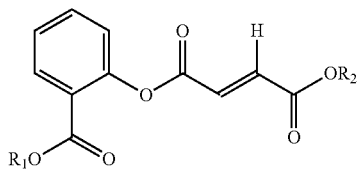

The $R_1$ in the structural formula (A) is one of $H^+$, $Na^+$, $K^+$ or $NH4^+$, $R_2$ is a fumaric acid ester.

The applicants further confirmed in their study that the above-mentioned structural formula, the fumaric acid ester of the $R_2$ group is one of methyl fumarate, mono-ethyl fumarate, mono-propyl fumarate, mono-isopropyl fumarate, mono-butyl fumarate, or mono-tertbutyl fumarate.

On the premise to determine the $R_2$ group, the applicants further confirmed that the salicyl fumarate derivative is methyl salicyl fumarate, the structure of which is:

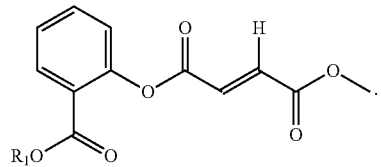

On the premise to determine the $R_2$ group, the applicants further confirmed that the salicyl fumarate derivative is ethyl salicyl fumarate, the structure of which is:

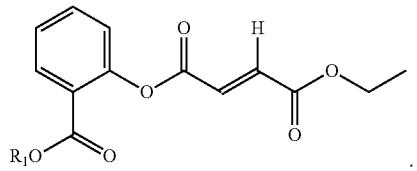

For all of the above salicyl fumarate derivatives, the $R_1$ group may be one of $H^+$, $Na^+$, $K^+$ or $NH4^+$. This depends on whether the applicants in aim of specific use of salicyl fumarate derivatives need to use the reaction between alkaline compounds and salicyl fumarate derivatives to generate salt forms. If the applicants do not use alkaline compounds to react with the salicyl fumarate derivative, then the $R_1$ will be a $H^+$. If the reaction is with NaOH solution, then $R_1$ group will be a $Na^+$. The other changes to the $R_1$ group are similar situations. Current research from the applicants show no direct effect from substituting $R_1$ group on the activity of salicyl fumarate derivative. Nonetheless, substituting $R_1$ changes the solubility of the salicyl fumarate derivative, therefore may affect the absorbability of salicyl fumarate derivative by the gastrointestinal tract.

As for the methodology for production of salicyl fumarate derivative, this method is carried out by esterification reaction. But because salicylic acid has two groups, hydroxyl and carboxyl groups, and under normal conditions, the stability of the carboxyl group is poorer; in order to achieve chemical directional reaction, the applicants designed the experiment to first use the esterification reaction of tert-butanol with salicylic acid to protect the carboxyl group. Then the product reacts with the mono-esterified fumarate. Finally, the target product is obtained by removing tert-butanol. The applicants provide methodology that includes the following steps:

1) The esterification reaction of tert-butanol and salicylic acid is carried out to protect the carboxyl group of salicylic acid to obtain intermediate product I;

2) The esterification reaction of intermediate product I and the fumaric acid derivative is carried out to obtain intermediate product II;

3) Remove tert-butanol from intermediate product II under acidic condition to obtain the target product III.

The chemical reaction formulae are as follows:

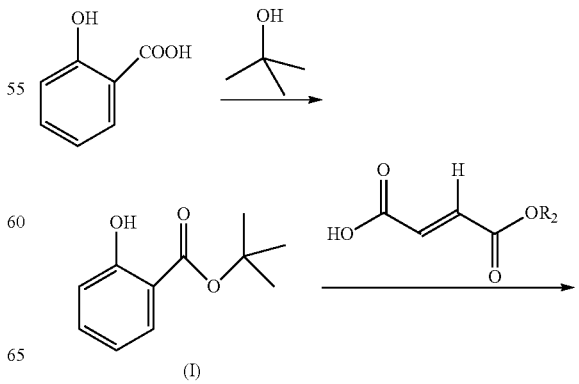

-continued

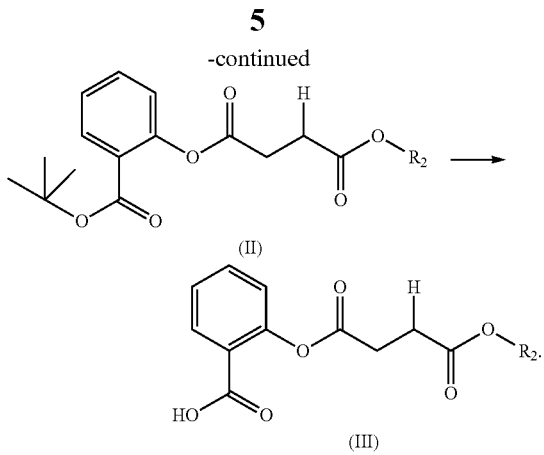

Through pharmacological experiments, the applicants demonstrated the application of salicyl fumarate derivatives as new therapeutic compounds in PD treatment.

The technology beneficial effect of the invention is: The present invention produces a salicyl fumarate derivative, which contains the general structural formula combining salicylic acid and fumarate derivative through esterification. The applicants through pharmacological experiments have verified that this kind of compounds has protective activity in the treatment of neurodegenerative diseases.

DESCRIPTION OF ATTACHED FIGURES

Figure 2:
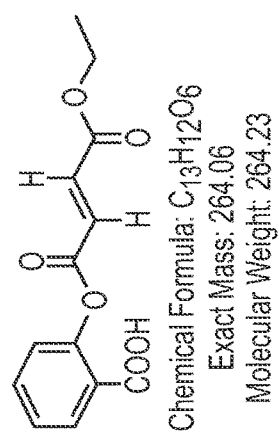
Figure 2:
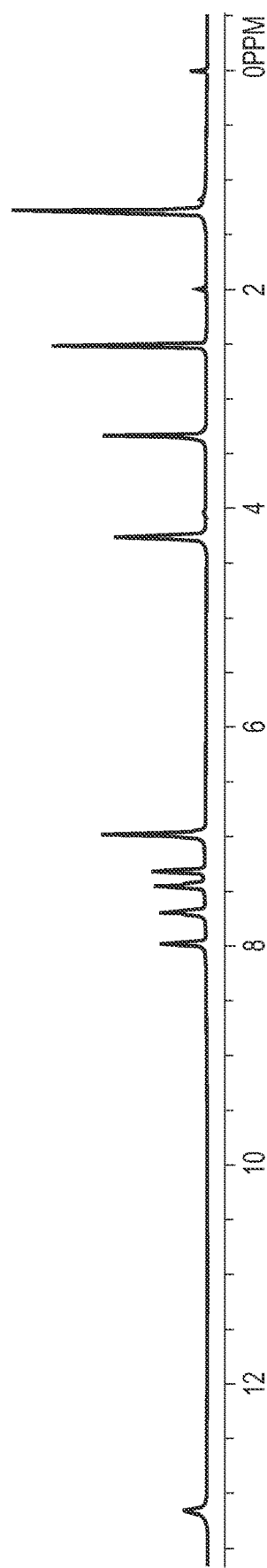
Figure 3:
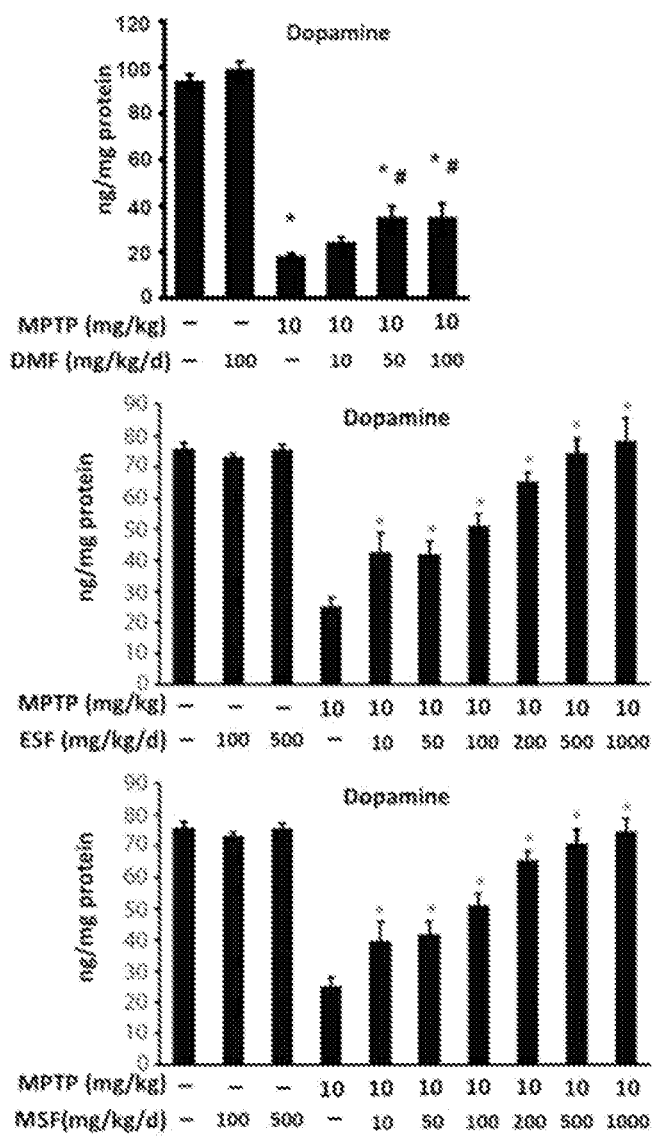
Figure 4:
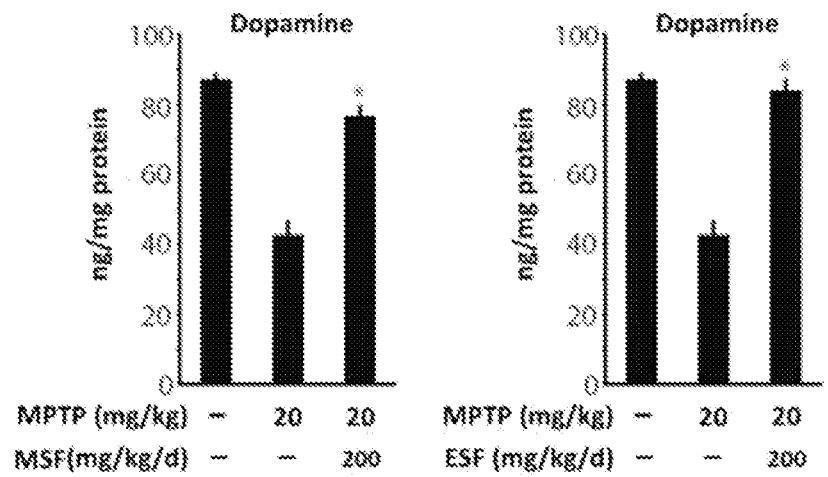
Figure 5:
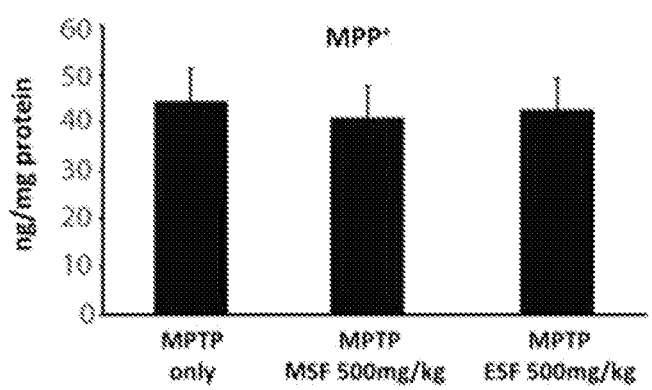
Figure 6:
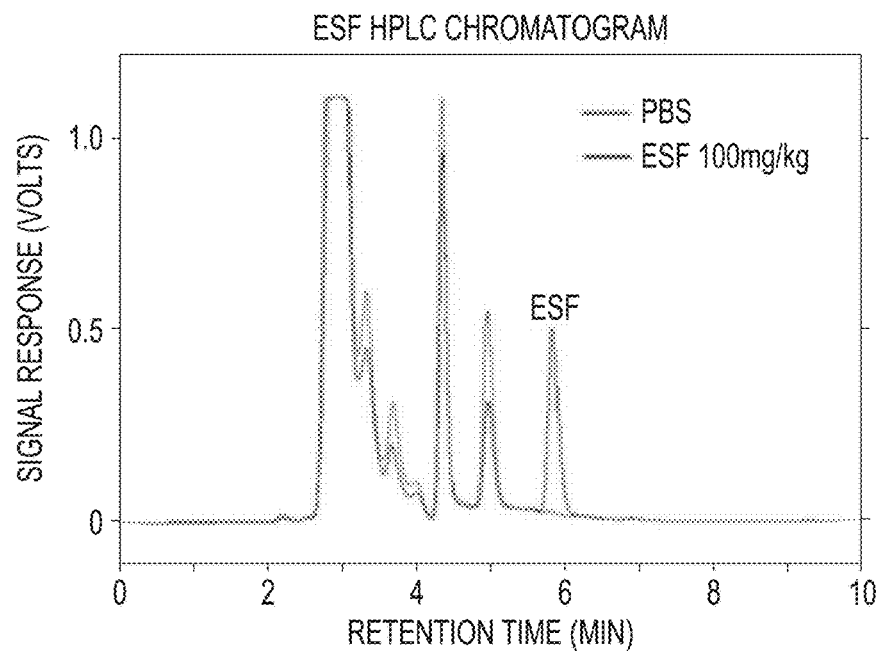
Figure 7:
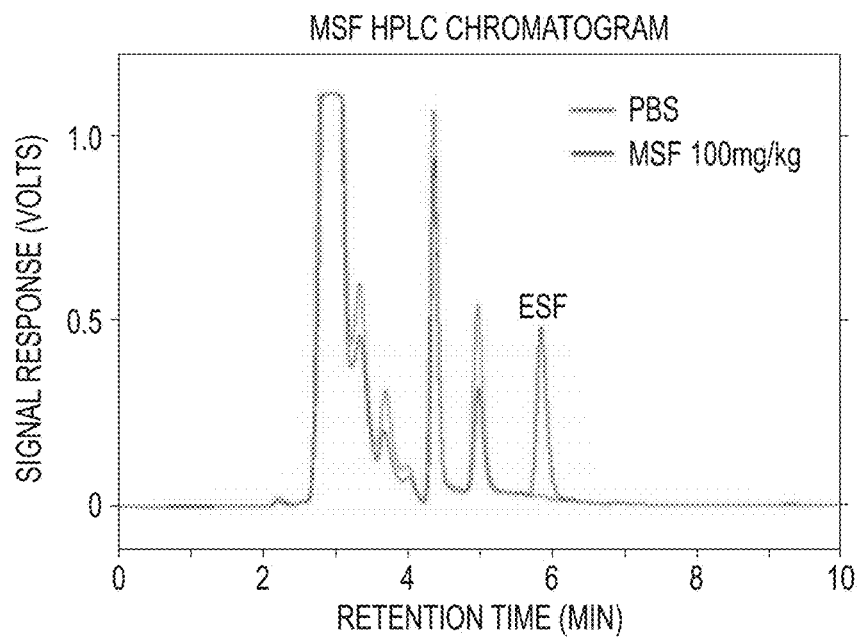
Figure 8:
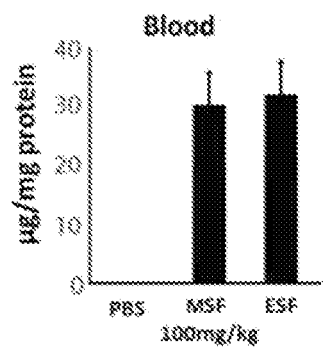
Figure 9:
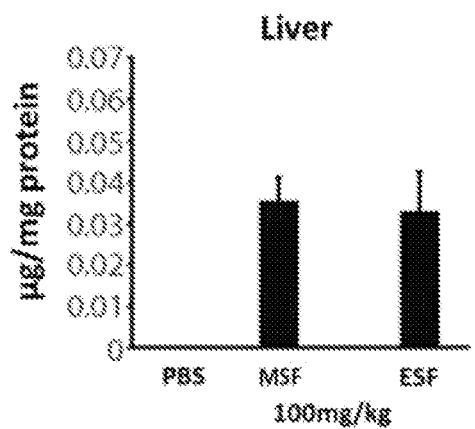
Figure 10:
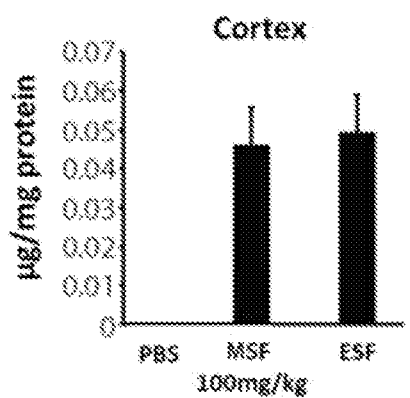
Figure 11:
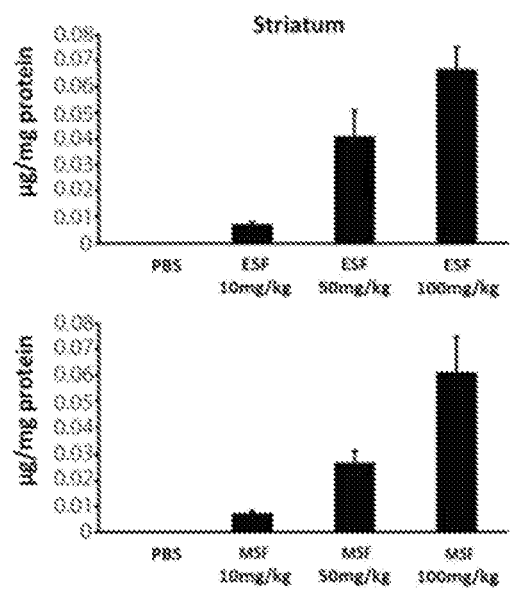
Figure 12:
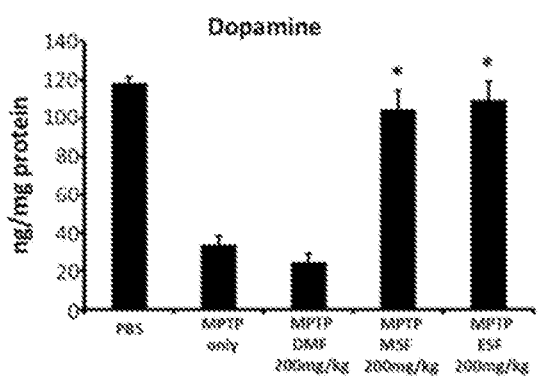
Figure 13:
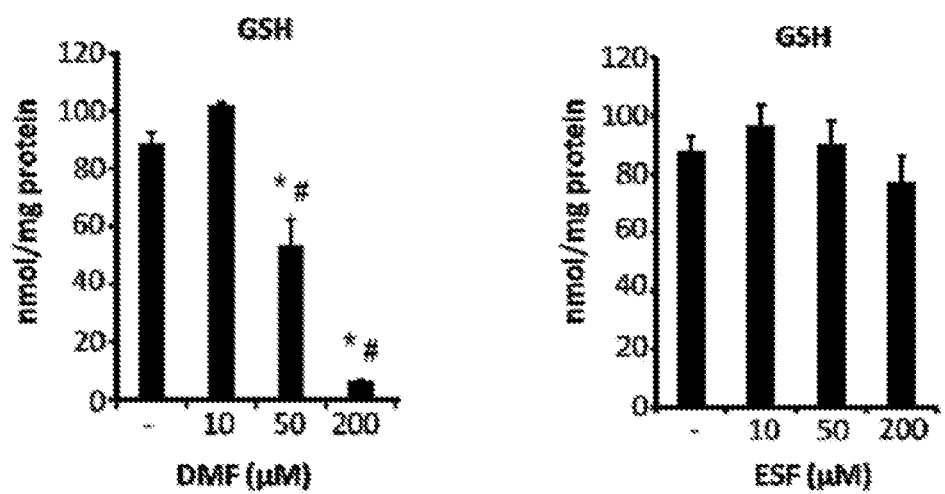

FIG. 1 MR spectrogram of Compound A (methyl salicyl fumarate);

FIG. 2 MR spectrogram of Compound B (ethyl salicyl fumarate);

FIG. 3 Dose response protection and safety study of MSF and ESF on MPTP-induced model of dopaminergic neuronal damage in mice;

FIG. 4 Protective effects of MSF and ESF on dopaminergic neurons in MPTP-induced model of chronic dopaminergic neuronal damage in mice;

FIG. 5 Effects of MSF and ESF on the concentrations of MPTP metabolites MPP+;

FIG. 6 HPLC Chromatogram of MSF in mouse blood sample;

FIG. 7 HPLC Chromatogram of ESF in mouse blood sample;

FIG. 8 Mouse blood drug concentrations with MSF and ESF dosage of 100 mg/kg;

FIG. 9 Mouse liver drug concentrations with MSF and ESF dosage of 100 mg/kg;

FIG. 10 Mouse brain drug concentrations with MSF and ESF dosage of 100 mg/kg;

FIG. 11 Under different MSF and ESF dosages, the drug concentrations in mouse striatum;

FIG. 12 The protective effect on dopaminergic neurons in Nrf2 knockout mice with MPTP-induced dopaminergic neuronal damage;

FIG. 13 Effects of MSF and ESF on intracellular glutathione concentrations in in vitro experiments;

In above figures, FIGS. 1 and 2 are NMR spectrograms generated by instrument work station; they were originally in color. After they were adjusted to black and white there were some text-and-image overlaps. This specific information has been documented in the Implementation Example 1 in the next section;

Chinese to English translations for FIGS. 3, 4, 5, 12, and 13;

Chinese to English translations for FIGS. 6 and 7;

Chinese to English translations for FIGS. 8, 9, and 10.

Specific Implementation Patterns

Implementation Example 1 Synthesis of Salicyl Fumarate Derivatives

1. Protecting the Carboxyl Group on the Salicylic Acid

Dissolve salicylic acid (45 g, 795.9 nmol, 1 equivalent weight) in dimethylformamide (DMF) (450 ml), under 0° C. (ice water bath) condition, add N'N-carbonyldiimidazole (63.5 g). At room temperature mix for 1 h, and at the same time slowly drip DBU (58.5 ml) and tert-butanol (63 ml). Then at room temperature mix for 2 h. After the reaction is done use LC-MS to detect (product spectrogram is illustrated in attached FIG. 1). Put reactants into water (500 ml), and use ethyl acetate to extract 3 times (3×800 ml). Combine with organic layers, then rinse 3 times (3×800 ml) with water; then rinse 1 time with saline (1000 ml); then dry with anhydrous $Na_2SO_4$; then filter; then concentrate the filtrate until no organic solvent residue is left. Purify the produced concentrate by silica gel column chromatography (petroleum ether:ethyl acetate=100:1 as mobile phase), obtaining the product (product 52 g, yield 82.5%). Product is light-yellow and oil-like (named: chemical compound A3). The chemical reaction formula is as follows:

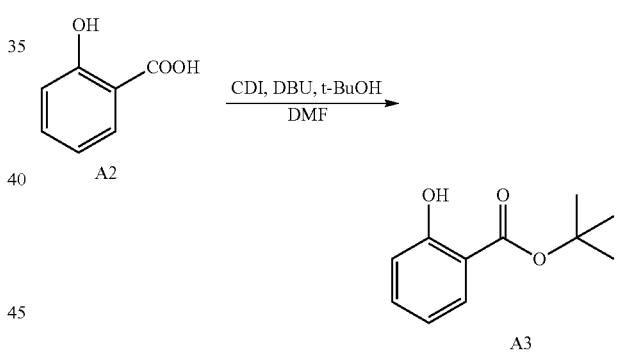

2. Esterification of Monomethyl Fumarate with Compound A3 (Compound A4)

Add DCM (100 ml) to monomethyl fumarate (10.4 g), then add the mixed solution of HATU (45.6 g) and DIEA (31 g). The reaction mixture is stirred for 30 minutes, then compound A3 (10 g) is added to the reaction mixture at room temperature and stirred for 16 hours at room temperature, LC-MS shows the reaction is complete. The reaction mixture is quenched with water (200 mL) and extracted with DCM (2×200 mL). Wash the combined organic layer with salt water (300 mL), then dry with anhydrous $Na_2SO_4$; then filter; then concentrate the filtrate until no organic solvent residue is left. Purify the produced concentrate by silica gel column chromatography (petroleum ether:ethyl acetate=30:1 as mobile phase), obtaining the product (product 12.6 g, yield 79.9 g). Product is light-yellow and oil-like (named: chemical compound A4). The chemical reaction formula is as follows:

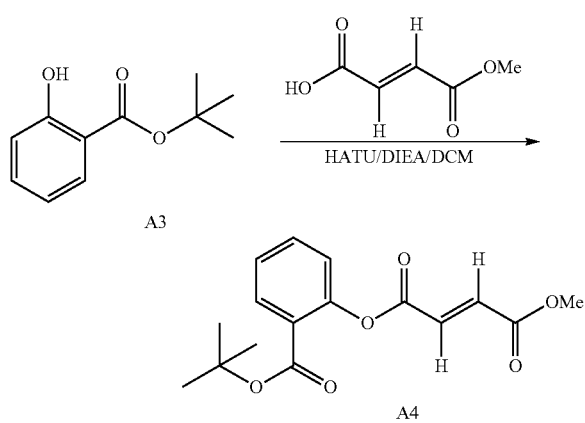

3. Preparation of Methyl Salicyl Fumarate (Compound A)

Under 0° C. (ice water bath) conditions, add compound A4 (5.6 g) to mixed solution of DCM (100 ml), 2N HCl and Et$_2$O (25 ml). The mixture reacts by stirring at room temperature overnight, TCL shows the reaction is complete. Remove the reaction solvent, add water (100 ml), then extract 3 times with DCM (3×150 ml). Combine organic layers, then rinse with salt water; dry with anhydrous Na$_2$SO$_4$. The product is purified by silica gel column chromatography (petroleum ether:ethyl acetate=2:1), and crude product is obtained. Mix the crude product with n-hexane (crystallization) overnight, filter to obtain pure product A (product 4.5 g, yield 98.4%); analyze with MR and MS assays, pure product A is identified as methyl salicyl fumarate. The reaction formula is as follows:

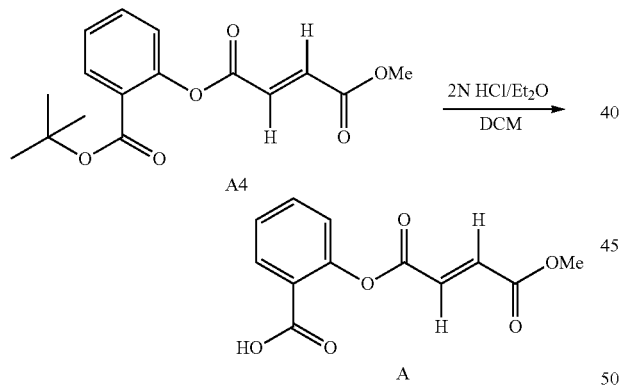

4. Esterification of Mono-Ethyl Fumarate with Compound A3 (Compound B2)

Add mono-ethyl fumarate (10.4 g) to DCM (100 ml), then add HATU (45.6 g) and DIEA (31 g) to mixed solution. The reaction mixture is stirred for 30 minutes, then compound A3 (10 g) is added to the reaction mixture at room temperature and stirred for 16 hours at room temperature, LC-MS shows the reaction is complete. The reaction mixture is quenched with water (200 mL) and extracted with DCM (2×200 mL). Wash the combined organic layer with salt water (300 mL), then dry with anhydrous Na$_2$SO$_4$; then filter; then concentrate the filtrate until no organic solvent residue is left. Purify the produced concentrate by silica gel column chromatography (petroleum ether:ethyl acetate=30:1 as mobile phase), obtaining the product (product 12.8 g, yield 79.9%). Product is light-yellow and oil-like (named: chemical compound B2). The chemical reaction formula is as follows:

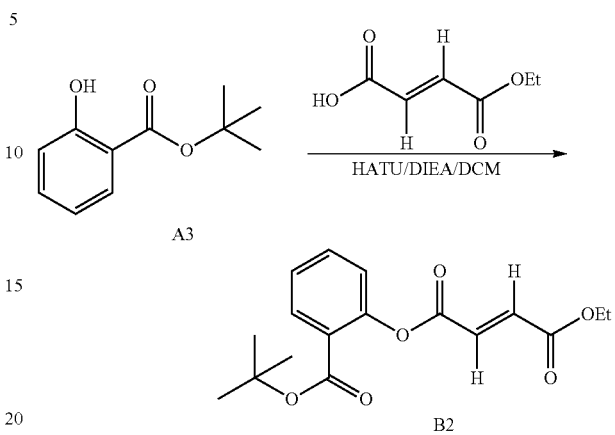

5. Preparation of Ethyl Salicyl Fumarate (Compound B)

Under 0° C. (ice water bath) conditions, add compound B2 (5.6 g) to mixed solution of DCM (100 ml), 2N HCl and Et$_2$O (25 ml). The mixture reacts by stirring at room temperature overnight. TCL shows the reaction is complete. Remove the reaction solvent, add water (100 ml), then extract 3 times with DCM (3×150 ml). Combine organic layers, then rinse with salt water; dry with anhydrous Na$_2$SO$_4$. The product is purified by silica gel column chromatography (petroleum ether:ethyl acetate=2:1), and crude product is obtained. Mix the crude product with n-hexane (crystallization) overnight, filter to obtain pure product A (product 4.0 g, yield 86.5%); analyze with MR and MS assays, pure product B is identified as ethyl salicyl fumarate. The reaction formula is as follows:

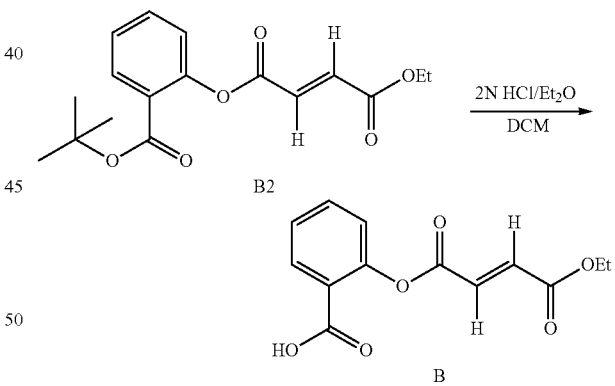

6. Analyzing Compound a and Compound B, the Specific Data are Below:

MR Spectrometry Assay

Compound A: $^1$H NMR (400 MHz, DMSO): δ13.18 (s, 1H), 7.98~7.96 (m, 1H), 7.71~7.67 (m, 1H), 7.46~7.42 (m, 1H), 7.32~7.30 (m, 1H), 6.99~6.98 (m, 2H), 3.80 (s, 3H); (NMR chromatogram shown in FIG. 1). MR spectrometry verifies compound A as methyl salicyl fumarate.

Compound B: $^1$H NMR (400 MHz, DMSO): δ13.16 (s, 1H), 7.98~7.96 (m, 1H), 7.70~7.67 (m, 1H), 7.45~7.41 (m, 1H), 7.31~7.29 (m, 1H), 6.97~6.96 (m, 2H), 4.27~4.22 (m, 2H), 1.29~1.26 (m, 3H); (NMR chromatogram shown in FIG. 2). MR spectrometry verifies compound B as ethyl salicyl fumarate.

7. The applicants used the same fore-mentioned synthesis routes to perform esterification of salicylic acid and fumarate esters. They obtained propyl salicyl fumarate (compound structural formula shown as C), isopropyl salicyl fumarate (compound structural formula shown as D), and butyl salicyl fumarate (compound structural formula shown as E) respectively. Considering the pharmacological activities of propyl salicyl fumarate, isopropyl salicyl fumarate, and butyl salicyl fumarate were lower than those of methyl salicyl fumarate and ethyl salicyl fumarate through preliminary experiments, the pharmacological studies of these three compounds will not be mentioned in this application.

However, from the synthesis routes of the 5 compounds, methyl salicyl fumarate, ethyl salicyl fumarate, propyl salicyl fumarate, isopropyl salicyl fumarate, and butyl salicyl fumarate, it can be known that if the carboxyl group on the salicylic acid can be effectively protected, salicyl fumarate derivatives can be synthesized. Therefore it is verified that the synthesis routes provided by the applicants are generally applicable for the effective synthesis of salicyl fumarate derivatives.

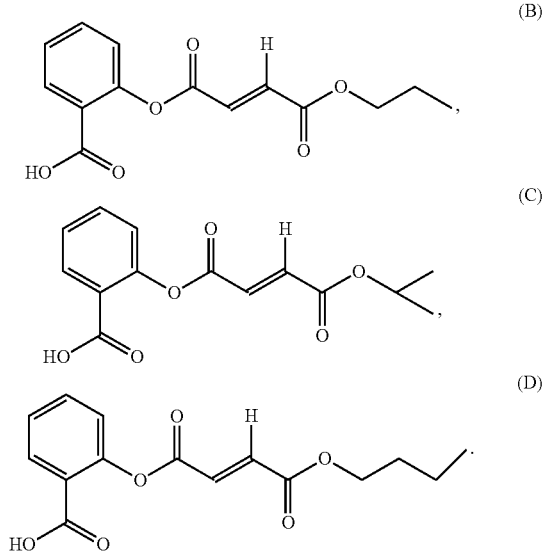

Implementation Example 2 the Protective Role of MSF and ESF on Dopaminergic Neurons Using MSF and ESF to conduct therapeutic studies with widely accepted MPTP-induced dopaminergic neuron-damaged PD mouse models. Dimethyl fumarate (DMF) was used as positive control drug, 6 dose groups were used for DME. For the experimental groups of MSF and ESF, 10 dose groups were used for each drug. 10 mice in each group. Both the experimental group and the control group used intraperitoneal administration. The control group was treated with DMF. The experimental groups were treated with different doses of ESF and MSF (as shown in FIG. 3). Statistically significant protective effects of dopamine neurons were found, and the dose-effect relationship was observed. The lowest dosage for protective effect (10 mg/kg/d), the optimal dosage (100-200 mg/kg/d), and the dosage where toxic effects began to appear (>500 mg/kg/d) were demonstrated. Compared to the results of DMF, MSF and ESF had more significant protective effects. Furthermore, the dosage where DMF showed protective effect (50 mg/kg/d) was higher than MSF and ESF, and the dosage where DMF showed toxic effect (>200 mg) was lower than MSF and ESF. Therefore, MSF and ESF have more effective and safer therapeutic dose windows (as shown in FIG. 3).

MSF and ESF (200 mg/kg/d) also showed significant dopamine neuron protection in models of chronic MPTP-induced dopamine neuron damage in mice, and the protection of dopamine neurons was close to a blank control level (as shown in FIG. 4).

The concentration of MPTP metabolite MPP+ in brain tissue was determined by HPLC. For the MPTP injected mouse model, the ESF (500 mg/kg) administered group and the blank group had the same MPP+ content in the striatum, excluding the possibility that MSF and ESF had an effect on the uptake and metabolism of MPTP in vivo and in the brain, confirming their neuroprotective effects (as shown in FIG. 5).

A reliable, high-performance liquid chromatography MSF and ESF analysis method (as shown in FIGS. 6 and 7) was established to determine the level of MSF and ESF in peripheral blood, liver, and brain tissue, demonstrating that MSF and ESF can enter the brain through the blood-brain barrier after intraperitoneal injection in mice. Furthermore, the molecular structure of MSF and ESF remains unchanged in the brain (as shown in FIG. 8, FIG. 9, FIG. 10, and FIG. 11), and it is inferred that MSF and ESF molecules produce neuroprotective pharmacological activities directly through their original molecule structures. Unlike the positive control drug DMF which worked differently. DMF needs to entering the body and quickly metabolizing into a form of single methyl metabolite monomethyl fumarate (MMF) which is the active form to produce pharmacological activity.

MSF and ESF have conventional fumaric acid (fumarate) activation target Nrf2 similar to the positive control drug DMF, which results in activating the mechanism of intracellular antioxidative stress. By performing MPTP experiments on transgenic mice with the Nrf2 gene knocked out, DMF lost the dopaminergic neuron protective effect due to the loss of its effective target, while MSF and ESF still show significant protective effects in this model (as shown in FIG. 12); thus confirming that MSF and ESF, in addition to acting on Nrf2 target, also act on another neuroprotective target. Inferring from the inclusion of salicyl in their molecule structure, this new target may be associated with anti-neuroinflammation.

The results of in vitro cell experiments showed that positive control drug DMF had the effect of depleting glutathione (GSH, endogenous antioxidant polypeptide), which may be the cause of its obvious toxicity and side effects. MSF and ESF have no effect on the concentration of glutathione in the cell (as shown in FIG. 13).

The invention claimed is:

1. A method comprising applying a salicyl fumarate derivative to drug production for the treatment of Parkinson's Disease, wherein the salicyl fumarate derivative is methyl salicyl fumarate having the below structural formula:

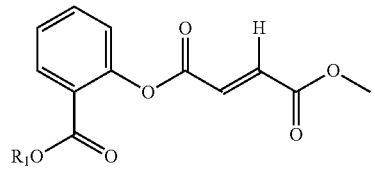

wherein $R_1$ is one of $H^{30}$, $Na^+$, $K^+$ or $NH^{4+}$.

2. A method comprising applying a salicyl fumarate derivative to drug production for the treatment of Parkinson's Disease, wherein the salicyl fumarate derivative is ethyl salicyl fumarate having the below structural formula:
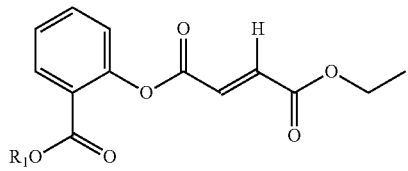
wherein $R_1$ is one of $H^+$, $Na^+$, $K^+$ or $NH^{4+}$.
* * * * *